US008318970B2

(12) United States Patent
Meisenburg et al.

(10) Patent No.: US 8,318,970 B2
(45) Date of Patent: Nov. 27, 2012

(54) PROCESS FOR PREPARING (METH)ACRYLATES OF $C_{10}$-ALCOHOL MIXTURES

(75) Inventors: Uwe Meisenburg, Mannheim (DE); Frank Hoefer, Bad Duerkheim (DE); Reinhold Schwalm, Wachenheim (DE); Nick Gruber, Mannheim (DE); Lothar Karrer, Pfungstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/867,511

(22) PCT Filed: Feb. 26, 2009

(86) PCT No.: PCT/EP2009/052241
§ 371 (c)(1),
(2), (4) Date: Aug. 13, 2010

(87) PCT Pub. No.: WO2009/106550
PCT Pub. Date: Sep. 3, 2009

(65) Prior Publication Data
US 2010/0317887 A1 Dec. 16, 2010

(30) Foreign Application Priority Data
Feb. 27, 2008 (EP) ..................................... 08102070

(51) Int. Cl.
*C07C 69/52* (2006.01)
(52) U.S. Cl. ........................................ 560/205; 560/129
(58) Field of Classification Search .................. None
See application file for complete search history.

(56) References Cited

U.S. PATENT DOCUMENTS 6,818,791 B2 * 11/2004 Martin et al. ................ 560/205
2004/0024241 A1    2/2004 Martin et al.

FOREIGN PATENT DOCUMENTS

| DE | 196 04 253 | 8/1997 |
|---|---|---|
| DE | 196 04 267 | 8/1997 |
| DE | 199 41 136 | 3/2001 |
| DE | 100 36 879 | 9/2001 |
| DE | 100 63 175 | 6/2002 |
| DE | 102 46 869 | 3/2003 |
| DE | 10 2007 001 540 | 8/2007 |
| JP | 04230239 | 8/1992 |
| JP | 04230239 A * | 8/1992 |
| JP | 05070403 | 3/1993 |
| JP | 05070404 | 3/1993 |
| WO | 02 055472 | 7/2002 |

OTHER PUBLICATIONS

International Search Report issued Sep. 15, 2009 in PCT/EP09/052241 filed Feb. 26, 2009.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

Process for preparing (meth)acrylates of $C_{10}$-alcohol mixtures, by reacting (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, in the presence of at least one acidic catalyst and of at least one polymerization inhibitor and in the presence of a solvent which forms an azeotrope with water, the azeotrope is distilled off and condensed, and the condensate splits into an aqueous phase and an organic phase, wherein a) the esterification is performed in a reactor with a circulation evaporator and
b) in the presence of a solvent, and
c) the crude product is purified by subsequent purifying distillation.

26 Claims, No Drawings

PROCESS FOR PREPARING (METH)ACRYLATES OF $C_{10}$-ALCOHOL MIXTURES

The present invention relates to a process for batchwise preparation of (meth)acrylates of $C_{10}$-alcohol mixtures by esterifying (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol.

In this document, the term (meth)acrylic acid is an abbreviated representation of methacrylic acid and/or acrylic acid, (meth)acrylic ester is an abbreviated representation of methacrylic ester and/or acrylic ester, and (meth)acrylate is an abbreviated representation of methacrylate and/or acrylate.

The isomer mixture of $C_{10}$-alcohols consists of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, these compounds being referred to hereinafter as "propylheptanol isomers" for short.

The polymers and copolymers prepared on the basis of (meth)acrylates of 2-propylheptanol and propylheptanol isomers are of great economic significance in the form of polymer dispersions. They find use, for example, as adhesives, paints, or textile, leather and papermaking assistants.

Japanese laid-open specification JP 05-070403 discloses the transesterification of methyl methacrylate with 2-propylheptanol in a 14-hour reaction in the presence of para-toluenesulfonic acid as a catalyst. The transesterification product is used to produce pressure-sensitive adhesives.

Japanese laid-open specification JP 05-070404 describes both the transesterification of methyl methacrylate with 2-propylheptanol to give 2-propylheptyl methacrylate and the esterification of methacrylic acid with 2-propylheptanol. The products are used as plasticizers in UV-curable resins.

DE 102 46 869 A1 discloses a process for continuously preparing (meth)acrylic esters by acid-catalyzed esterification of (meth)acrylic acid, preferably using alcohols comprising from 6 to 12 carbon atoms for the esterification.

The processes disclosed in DE 196 04 253 A1 and DE 196 04 267 A1 likewise involve the continuous preparation of (meth)acrylic esters by acid-catalyzed esterification of (meth)acrylic acid. However, alkanols having from 1 to 8 carbon atoms are used for the esterification.

DE 100 36 879 A1 discloses a continuous process for preparing esters of (meth)acrylic acid by esterifying (meth)acrylic acid with $C_6$-$C_{10}$-alkanols.

The batchwise preparation of (meth)acrylic esters by esterification is described in WO 02/055472 A1. What is disclosed is the esterification of (meth)acrylic acid with higher mono- or polyhydric alcohols, polyether alcohols or polyester alcohols. The higher esters of (meth)acrylic acid which are obtained by this process and preferably have a molecular weight of >200 g/mol cannot be purified by distillation.

The literature cited above discloses exclusively (meth)acrylates of 2-propylheptanol as the $C_{10}$-alcohol component; isomer mixtures of 2-propylheptanol are not described. In addition, the processes are essentially processes for continuously preparing the (meth)acrylates.

German laid-open specification DE 10 2007 001 540 A1 discloses $C_{10}/C_6$ ester mixtures based on 2-propylheptanol, which are accordingly a mixture of esters of an aliphatic or aromatic di- or tricarboxylic acid with a $C_{10}$-alcohol component composed of 2-propylheptanol, and esters of an aliphatic or aromatic di- or tricarboxylic acid with a $C_6$-alcohol component composed of n-hexanol.

It was therefore an object of the present invention to provide a further, alternative process for preparing (meth)acrylates of $C_{10}$-alcohol mixtures which comprise especially 2-propylheptyl (meth)acrylate as the main isomer, with which the (meth)acrylates of $C_{10}$-alcohol mixtures are obtained in high yields and in high purities. In addition, products with low color numbers should result.

The object is achieved by a process for preparing (meth)acrylates of $C_{10}$-alcohol mixtures, by reacting (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, in the presence of at least one acidic catalyst and of at least one polymerization inhibitor and in the presence of a solvent which forms an azeotrope with water, the azeotrope is distilled off and condensed, and the condensate splits into an aqueous phase and an organic phase, wherein a) the esterification is performed in a reactor with a circulation evaporator and
b) in the presence of a solvent, and
c) the crude product is purified by subsequent purifying distillation.

In the process according to the invention, a $C_{10}$-alcohol mixture which comprises 2-propylheptanol as the main isomer is used. In the context of the present invention, the term "main isomer" is understood to mean a content of 2-propylheptanol of up to 100% by weight, based on the total weight of the $C_{10}$-alcohol mixture. The content of 2-propylheptanol is generally at least 50% by weight, preferably from 60 to 98% by weight and more preferably from 80 to 95% by weight, especially from 85 to 95% by weight, based in each case on the total weight of the $C_{10}$-alcohol mixture.

In addition to 2-propylheptanol as the main isomer, the $C_{10}$-alcohol mixture also comprises at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol. These compounds are referred to hereinafter as "propylheptanol isomers" for short. The presence of other isomers of the 2-propylheptanol component—for example originating from those alcohols 2-ethyl-2,4-dimethylhexanol, 2-ethyl-2-methylheptanol and/or 2-ethyl-2,5-dimethylhexanol, which are isomeric to 2-propylheptanol—in the $C_{10}$-alcohol mixture is possible but, if at all, they are present only in traces.

For the preparation of 2-propylheptanol and propylheptanol isomers, reference is made at this point to German laid-open specification DE 10 2007 001 540 A1 and the literature cited therein.

Suitable mixtures of 2-propylheptanol with the propylheptanol isomers comprise, for example, those composed of from 60 to 98% by weight of 2-propylheptanol, from 1 to 15% by weight of 2-propyl-4-methylhexanol, from 0.01 to 20% by weight of 2-propyl-5-methylhexanol and from 0.01 to 24% by weight of 2-isopropylheptanol, where the sum of the proportions of the individual constituents does not exceed 100% by weight. The proportions of the individual constituents preferably add up to 100% by weight.

Further suitable mixtures of 2-propylheptanol with the propylheptanol isomers comprise, for example, those composed of from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol and from 0.1 to 2% by weight of 2-isopropyl-5-methylhexanol, where the sum of the proportions of the individual constituents does not exceed 100% by weight. The proportions of the individual constituents preferably add up to 100% by weight.

Preferred mixtures of 2-propylheptanol with the propylheptanol isomers comprise those with from 85 to 95% by weight of 2-propylheptanol, from 5 to 12% by weight of 2-propyl-4-methylhexanol, from 0.1 to 2% by weight of 2-propyl-5-methylhexanol and from 0.01 to 1% by weight of 2-isopropylheptanol, where the sum of the proportions of the individual constituents does not exceed 100% by weight. The proportions of the individual constituents preferably add up to 100% by weight.

Preferred mixtures of 2-propylheptanol with the propylheptanol isomers further comprise those composed of from 80 to 92% by weight of 2-propylheptanol, from 6 to 12% by weight of 2-propyl-4-methylhexanol, from 5 to 13% by weight of 2-propyl-5-methylhexanol, from 0.1 to 2% by weight of 2-isopropylheptanol, from 0.1 to 1% by weight of 2-isopropyl-4-methylhexanol and from 0.1 to 1% by weight of 2-isopropyl-5-methylhexanol, where the sum of the proportions of the individual constituents does not exceed 100% by weight. The proportions of the individual constituents preferably add up to 100% by weight.

The composition of the (meth)acrylates of $C_{10}$-alcohol mixtures which are prepared by the process according to the invention corresponds virtually to the composition of the propylheptanol isomer mixtures used in the esterification to prepare them.

The mixtures of 2-propylheptanol with the propylheptanol isomers may comprise, as impurities caused by the preparation process, also traces of n-pentanol, 2-methylbutanol and/or 3-methylbutanol. The contents of these alcohols are generally in each case not more than 0.5% by weight based on the total weight of the $C_{10}$-alcohol mixture.

The process according to the invention is advantageous since a high degree of esterification is attained and high yields are achieved. In addition, no significant polymer formation occurs in the course of esterification or workup, and the end product is substantially colorless.

The water formed in the esterification, which forms an azeotrope with the solvent, is discharged via a column attached to the reactor and condensed.

The condensate obtained (azeotrope) splits into an aqueous phase, which is discharged and advantageously worked up (reextraction of the acid present), and a solvent phase, which is recycled as reflux into the column and if appropriate partly into the reactor and/or evaporator, as described in DE 199 41 136 A1 and DE 100 63 175 A1.

A reextraction of the (meth)acrylic acid present is preferably effected with the solvent used as the extractant, for example with cyclohexane at a temperature between 10 and 40° C. and a ratio of aqueous phase to extractant of 1:5-30, preferably 1:10-20. The acid present in the extractant can preferably be conducted directly into the esterification.

After the esterification has ended, the hot reaction mixture is cooled rapidly and if appropriate diluted with solvent.

Subsequently, the solvent is removed by distillation from the target ester.

Finally, the crude product which comprises the target ester is purified by distillation, so as to obtain an end product with particularly low color number.

The process according to the invention consists essentially of the following stages:

1) Esterification

The esterification apparatus consists of a reactor with a circulation evaporator and an attached distillation column with condenser and phase separation vessel.

The reactor may, for example, be a reactor with jacket heating and/or internal heating coils. Preference is given to using a reactor with external heat exchanger and natural or forced circulation (using a pump). In the case of natural circulation, the cycle stream is accomplished without mechanical aids.

Suitable circulation evaporators are known to those skilled in the art and are described, for example, in R. Billet, Verdampfertechnik [Evaporator technology], HTB-Verlag, Bibliographisches Institut Mannheim, 1965, 53. Examples of circulation evaporators are tube bundle heat exchangers, plate heat exchangers, etc.

It will be appreciated that it is also possible for a plurality of heat exchangers to be present in the circulation system.

The distillation column is of a design known per se and has the customary internals. The column internals used may in principle be all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles or braids.

In general, from 5 to 20 theoretical plates are sufficient.

The condenser and the separating vessel are of conventional design.

(Meth)acrylic acid and the $C_{10}$-alcohol mixture, which comprises 2-propylheptanol as the main isomer, are generally used in equivalent amounts, but it is also possible to use a deficiency or excess of (meth)acrylic acid.

Both (meth)acrylic acid and (meth)acrylic esters are polymerizable compounds. Therefore, sufficient inhibition of polymerization should be ensured in the process step of esterification. Suitable polymerization inhibitors are disclosed further down. Among the stabilizers mentioned there, especially copper(II) chloride is suitable for the esterification.

Preference is given to establishing an excess of (meth)acrylic acid per hydroxyl group (equivalent) to be esterified of 5-100 mol %, preferably 5-50 mol % and more preferably 5-10 mol %.

Useful esterification catalysts include the customary mineral acids and sulfonic acids, preferably sulfuric acid, phosphoric acid, alkylsulfonic acids (e.g. methanesulfonic acid, trifluoromethanesulfonic acid) and arylsulfonic acids (e.g. benzene-, p-toluene-, or dodecylbenzenesulfonic acid) or mixtures thereof, but acidic ion exchangers or zeolites are also conceivable.

Particular preference is given to sulfuric acid, methanesulfonic acid and p-toluene-sulfonic acid, or mixtures thereof.

They are used generally in an amount of 0.1-5% by weight, based on the esterification mixture, preferably 0.5-5% by weight and more preferably 1-4% by weight.

If required, the esterification catalyst can be removed from the reaction mixture with the aid of an ion exchanger. The ion exchanger can be added directly to the reaction mixture and then filtered off, or the reaction mixture can be passed through an ion exchanger bed.

Preference is given to leaving the esterification catalyst in the reaction mixture.

Suitable solvents for azeotropic removal of the water of reaction are in particular aliphatic, cycloaliphatic and aromatic hydrocarbons or mixtures thereof.

Preference is given to employing n-pentane, n-hexane, n-heptane, cyclohexane, methylcyclohexane, benzene, toluene or xylene. Particular preference is given to cyclohexane, methylcyclohexane and toluene.

The amount used is, for example, 10-200% by weight, preferably 20-100% by weight, more preferably 30-100% by weight, based on the sum of (meth)acrylic acid and $C_{10}$-alcohol mixture.

The reaction temperature is generally 60-140° C., preferably 70-110° C., most preferably 75-100° C. The starting temperature is generally below 100° C., preferably below 90° C. and more preferably below 80° C. In general, the end temperature of the esterification is 5-30° C. higher than the starting temperature. The temperature of the esterification can be determined and controlled by varying the solvent concentration in the reaction mixture, as described in DE 199 41 136 A1 and DE 100 63 175 A1.

The esterification can be carried out at ambient pressure or else at elevated pressure or reduced pressure; preference is given to working at standard pressure.

The reaction time is generally from 30 minutes to 10 hours, preferably 1-6 hours and more preferably 2-4 hours.

The reactants (meth)acrylic acid and $C_{10}$-alcohol mixture which comprises 2-propyl-heptanol as the main isomer, and also the other components such as solvents, polymerization inhibitor (mixture) and catalyst, can be added as desired.

In a preferred embodiment, solvent and the $C_{10}$-alcohol mixture are initially charged in the reactor at least partly, preferably completely, and heated. As soon as the circulation is in operation, the remaining components (meth)acrylic acid, polymerization inhibitor (mixture) and catalyst can be metered in together or separately from one another. The metered addition is effected generally within 0.5-5 hours, continuously or in portions.

The usable (meth)acrylic acid is not restricted and may, in the case of crude (meth)acrylic acid, comprise, for example, the following components:

| | |
|---|---|
| (meth)acrylic acid | 90-99.9% by weight |
| acetic acid | 0.05-3% by weight |
| propionic acid | 0.01-1% by weight |
| diacrylic acid | 0.01-5% by weight |
| water | 0.05-5% by weight |
| aldehydes | 0.01-0.3% by weight |
| inhibitors | 0.01-0.1% by weight |
| maleic acid/anhydride | 0.001-0.5% by weight |

The crude (meth)acrylic acid used is generally stabilized with 100-600 ppm, preferably with 200-500 ppm, of one of the polymerization inhibitors mentioned below, preferably phenothiazine or hydroquinone monomethyl ether, or other stabilizers which enable comparable stabilization.

It will be appreciated that it is also possible to use glacial (meth)acrylic acid with, for example, the following purity:

| | |
|---|---|
| (meth)acrylic acid | 99.7-99.99% by weight |
| acetic acid | 50-1000 ppm by weight |
| propionic acid | 10-500 ppm by weight |
| diacrylic acid | 10-500 ppm by weight |
| water | 50-1000 ppm by weight |
| aldehydes | 1-500 ppm by weight |
| inhibitors | 1-300 ppm by weight |
| maleic acid/anhydride | 1-200 ppm by weight |

The glacial (meth)acrylic acid used is generally stabilized with 100-400 ppm, preferably with 200-300 ppm, of one of the polymerization inhibitors mentioned below, preferably phenothiazine or hydroquinone monomethyl ether, or other stabilizers which enable comparable stabilization.

The water formed in the reaction is removed from the reaction mixture continuously as an azeotrope with the solvent via the column attached to the reactor and condensed, and the condensate splits into a water phase and an organic phase.

The aqueous phase of the condensate, which generally comprises 0.1-10% by weight of (meth)acrylic acid, is removed and discharged. Advantageously, the (meth)acrylic acid present therein can be extracted with an extractant, for example with cyclohexane, at a temperature between 10 and 40° C. and a ratio of aqueous phase to extractant of 1:5-30, preferably 1:10-20, and recycled into the esterification.

The organic phase can be recycled fully or partly as reflux into the column and any excess remainder can be recycled into the reactor. A portion of this phase can, in the case of use of natural circulation, if appropriate be introduced into the heat exchanger of the circulation system of the reactor to promote the natural circulation, preferably at least 10% by weight of the organic phase, more preferably at least 15% by weight and most preferably at least 20% by weight.

An advantageous variant consists in passing the organic phase (solvent phase) into a reservoir vessel and withdrawing from this vessel the amount of solvent required in each case to maintain the reflux, for introduction into the circulation evaporator, and as the solvent for reaction and extraction.

To further promote the circulation, it is possible to pass an inert gas, preferably an oxygenous gas, more preferably air or a mixture of air and nitrogen (lean air) into the circulation system, for example in amounts of 0.1-1 $m^3/m^3h$, preferably 0.2-0.8 $m^3/m^3h$ and more preferably 0.3-0.7 $m^3/m^3h$, based on the volume of the reaction mixture.

The course of the esterification can be monitored by monitoring the amount of water discharged and/or the decrease in the (meth)acrylic acid concentration in the reactor.

The reaction can be ended, for example, as soon as 90% of the theoretically expected amount of water has been discharged by the solvent, preferably at least 95% and more preferably at least 98%.

After the esterification has ended, the reaction mixture is cooled rapidly to a temperature of from 10 to 30° C. in a customary manner, and if appropriate a target ester concentration of 60-80% is established by adding solvent.

2) Preliminary Wash and Neutralization

The reaction mixture is, if appropriate, treated in a washing apparatus with water or a 5-30% by weight, preferably 5-20% by weight, more preferably 5-15% by weight, sodium chloride solution, potassium chloride solution, ammonium chloride solution, sodium sulfate solution or aluminum sulfate solution, preferably sodium chloride solution.

The ratio of reaction mixture:wash liquid is generally 1:0.1-1, preferably 1:0.2-0.8, more preferably 1:0.3-0.7.

The wash can be carried out, for example, in a stirred vessel or in another conventional apparatus, for example in a column or mixer-settler apparatus.

In terms of process technology, for a wash in the process according to the invention, it is possible to use all extraction processes, extraction apparatus, washing processes and washing apparatus known per se, for example those which are described in Ullmann's Encyclopedia of Industrial Chemistry, 6th ed, 1999 Electronic Release, chapter: Liquid—Liquid Extraction—Apparatus. For example, they may be single-stage or multistage, preferably single-stage, extractions, and also those in cocurrent or countercurrent mode.

The preliminary wash is preferably used when (some of) the inhibitors used are metal salts, preferably copper or copper salts.

The organic phase of the preliminary wash, which still comprises small amounts of catalyst and the majority of excess (meth)acrylic acid, is neutralized with a 5-25% by weight, preferably 5-20% by weight, more preferably 5-15% by weight, aqueous solution of a base, for example sodium hydroxide solution, potassium hydroxide solution, sodium hydrogencarbonate, sodium carbonate, potassium hydrogencarbonate, calcium hydroxide, aqueous ammonia or potassium carbonate, to each of which may if appropriate be added 5-15% by weight of sodium chloride, potassium chloride, ammonium chloride or ammonium sulfate, preferably neutralized with sodium hydroxide solution or sodium hydroxide/sodium chloride solution.

The base is added in such a way that the temperature in the apparatus does not rise above 35° C., and is preferably between 20 and 35° C., and the pH is 10-14. The heat of neutralization is removed, if appropriate, by cooling the vessel with the aid of internal cooling coils or by means of jacket cooling.

The ratio of reaction mixture:neutralization liquid is generally 1:0.1-1, preferably 1:0.2-0.8, more preferably 1:0.3-0.7.

With regard to the apparatus, the same applies as was stated above.

Optionally, to remove base or salt traces from the neutralized reaction mixture, a subsequent wash may be advantageous, which can be carried out analogously to the preliminary wash.

3) Solvent Distillation

The washed reaction mixture is admixed with such an amount of storage stabilizer, preferably hydroquinone monomethyl ether, that, after removal of the solvent, 100-500 ppm, preferably 200-500 ppm and more preferably 200-400 ppm thereof are present in the target ester.

The majority of solvent is removed by distillation, for example, in a stirred tank with jacket heating and/or internal heating coils under reduced pressure, for example at 20-700 mbar, preferably from 30 to 500 mbar and more preferably from 50 to 150 mbar, and a temperature of 40-80° C.

It will be appreciated that the distillation can also be effected in a falling-film or thin-film evaporator. To this end, the reaction mixture, preferably repeatedly in circulation, under reduced pressure, is conducted through the apparatus, for example, at 20-700 mbar, preferably from 30 to 500 mbar, more preferably 50-150 mbar, and a temperature of 40-80° C.

Advantageously, an inert gas, preferably an oxygenous gas, more preferably air or a mixture of air and nitrogen (lean air) can be introduced into the distillation apparatus, for example 0.1-1 $m^3/m^3h$, preferably 0.2-0.8 $m^3/m^3h$ and more preferably 0.3-0.7 $m^3/m^3h$, based on the volume of the reaction mixture.

The residual solvent content in the residue after distillation is generally below 5% by weight, preferably 0.5-5% by weight.

The solvent removed is condensed and preferably reused.

4) Purifying Distillation

According to the invention, the target ester is isolated as the top product in a further distillation step from the bottoms obtained below the solvent distillation and stabilized with at least one of the polymerization inhibitors mentioned below. Among the stabilizers mentioned there, especially hydroquinone monomethyl ether and phenothiazine are suitable for the purifying distillation.

The rectification column usable for this distillation step is of a known design, for example columns with random packing, columns with structured packing or tray columns, and has separating internals (for example bubble-cap, sieve or dual-flow trays) or comprises beds or structured packing. These customary internals are as described in stage 1) (esterification) and have preferably from 10 to 20 theoretical plates. Thin-film evaporators are also useful. Evaporators and condensers are likewise of conventional design (see stage 1, esterification).

The target ester is preferably obtained at a bottom temperature of 100-140° C., preferably of 110-130° C., and a top pressure of from 1 to 100 mbar, preferably from 1 to 50 mbar, more preferably from 1 to 10 mbar and especially from 1 to 5 mbar.

For stabilization, it is possible to spray a solution of 0.05-0.5% hydroquinone monomethyl ether or another similarly effective storage stabilizer into the condenser, the amount selected being such that the condensate has a storage stabilizer concentration of 10-20 ppm. A portion of the condensate, preferably 10-20%, can be fed back to the column as reflux.

The target ester obtained, which comprises 2-propylheptyl (meth)acrylate as the main isomer, according to gas chromatography analysis, has a purity of at least 98.5%, preferably at least 99.0% and more preferably at least 99.5%.

The bottom product of the purifying distillation, which consists principally of residual target ester, Michael addition products, stabilizer and polymers, can be passed into a residue distillation and/or residue cleavage.

It will be appreciated that it is also possible to combine the distillation units of the solvent distillation (stage 3) and the purifying distillation. In this case, the pure target ester is discharged via a side draw, preferably in gaseous form, in the lower column region, preferably in the lower half, more preferably in the lower third, condensed and stabilized as described above.

The target esters prepared by the process according to the invention, which comprise 2-propylheptyl (meth)acrylate as the main isomer, are notable for a high purity and a low APHA color number (determined to DIN-ISO 6271). The APHA color number is preferably below 50, more preferably below 25 and more preferably below 10.

Surprisingly, the process according to the invention can purify (meth)acrylates of $C_{10}$-alcohol mixtures, which comprise 2-propylheptanol as the main isomer, by a purifying distillation, even though they comprise higher acrylates which are known to be obtainable by distillation only with difficulty, if at all.

(Meth)acrylic acid and (meth)acrylic esters of $C_{10}$-alcohol mixtures are polymerizable compounds. Therefore, sufficient inhibition of polymerization should be ensured in all process steps. Undesired polymerization is a safety hazard owing to the large amount of heat released.

Therefore, in the process according to the invention, both the esterification reaction and the thermal separations are preferably carried out in the presence of customary amounts of polymerization inhibitors known per se. In general, based on the α,β-monoethylenically unsaturated monomers, per individual substance, from 1 to 10 000 ppm, preferably from 10 to 5000 ppm, more preferably from 30 to 2500 ppm and especially from 50 to 1500 ppm, of a suitable stabilizer are used.

Suitable stabilizers may, for example, be N-oxides (nitroxyl or N-oxyl radicals, i.e. compounds which have at least one >N—O. group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4"-tris(2,2,6,6-tetramethylpiperidine N-oxyl) phosphite or 3-oxo-2,2,5,5-tetramethyl-pyrrolidine N-oxyl; mono- or polyhydric phenols which may have one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, for example p-aminophenol; nitrosophenols, for example p-nitrosophenol; alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example α-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine, where the alkyl radicals may be the same or different and each consist independently of from 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicyladoxime, phosphorus compounds, for example triphenylphosphine, triphenyl phosphite, triethyl phosphite, hypophosphorous acid or alkyl esters of phosphorous acids; sulfur compounds, for example diphenyl sulfide or phenothiazine; metal salts such as copper or manganese, cerium, nickel, chromium salts, for example chlorides, sulfates, salicylates, tosylates, acrylates or acetates, for example copper acetate, copper(II) chloride, copper salicylate, cerium (III) acetate or cerium(III) ethylhexanoate, or mixtures thereof.

The polymerization inhibitor (mixture) used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

Very particular preference is given to using phenothiazine and/or hydroquinone monomethyl ether (MEHQ) as the polymerization inhibitor.

Preference is given to using the polymerization inhibitor (mixture) in the form of an aqueous solution.

To further support the stabilization, an oxygenous gas may be present, preferably air or a mixture of air and nitrogen (lean air).

In the process step of esterification, the oxygenous gas is preferably metered into the bottom region of the column and/or into a circulation evaporator.

The (meth)acrylates, prepared in accordance with the invention, of $C_{10}$-alcohol mixtures which comprise 2-propylheptanol as the main isomer find use, for example, as monomers or comonomers in the preparation of dispersions which are used, inter alia, as adhesives, paints, or textile, leather and papermaking assistants.

In addition, the (meth)acrylates of $C_{10}$-alcohol mixtures prepared by the process according to the invention, which comprise 2-propylheptanol as the main isomer, may find use as a comonomer in polymers, which are in turn used as an additive for fuel oils and lubricants and especially as a cold flow improver in fuel oils. Such a use is disclosed, for example, in European application EP 06 124 356.4.

The example which follows is intended to illustrate the properties of the invention, but without restricting it.

Unless stated otherwise, percent always means percent by weight, and parts always parts by weight.

EXAMPLE

In an esterification apparatus (1 l 4-neck flask with internal thermometer, reflux condenser and water separator), the esterification of acrylic acid with 2-propylheptanol was carried out. It was initially charged with 132 ml of cyclohexane, 94.8 g (0.6 mol) of 2-propylheptanol (comprised approx. 88.3% 2-propylheptanol as the main isomer; as secondary isomers, approx. 9.7% 4-methyl-2-propylhexanol and approx. 1.9% 5-methyl-2-propylhexanol were present) and 1.5 ml of 50% hypophosphorous acid, which were stirred at 60° C. for 2 hours. Subsequently, 3 ml of stabilizer solution (1.25 g of hydroquinone monomethyl ether (MEHQ) and 3.25 g of hypophosphorous acid dissolved in 37.5 g of water), 0.3 ml of 20% copper(II) chloride solution and 31.8 g (0.66 mol) of acrylic acid (stabilized with 200 ppm of MEHQ) were added. The mixture was heated under an air atmosphere, and 2.4 ml of 98% methanesulfonic acid were added at an internal temperature of 75° C. After boiling under reflux for 2 hours, in the course of which water was removed continuously, the reaction solution was cooled.

60 ml of 7.5% sodium chloride solution were added to the resulting clear solution. 40 ml of 12.5% sodium hydroxide solution were used to establish a pH of 13.

After extraction by shaking, the cyclohexane phase was removed, dried over sodium sulfate, filtered and admixed with 24.5 g (200 ppm) of MEHQ. Subsequently, the solvent was removed under reduced pressure. A clear liquid was obtained.

2-Propylheptyl acrylate was obtained in a yield of 124 g (97%) and a purity of >95%, and with an APHA color number of 11.

The crude product was purified by distillation; the parameters and results of the distillation are compiled in table 1.

TABLE 1

Parameters and results of the distillation

| Fraction | Yield [g] | Distillation temperature [° C.] | Pressure [mbar] | APHA color number |
|---|---|---|---|---|
| Crude product | 124.0 | — | — | 11 |
| Fraction 1 | 30.8 | 81-83 | 0.4-0.5 | — |
| Fraction 2 | 42.9 | 83-85 | 0.5 | — |
| Fraction 3 | 35.5 | 85-86 | 0.5 | — |
| Σ Fractions 1-3 | 109.2 | — | — | 8 |

The target ester 2-propylheptyl acrylate was obtained in high purity (>99%) and with low APHA color number.

The invention claimed is:

1. A process for batchwise preparing (meth)acrylates of $C_{10}$-alcohol mixtures, comprising:
reacting (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, in the presence of at least one acidic catalyst selected from the group consisting of a mineral acid and a sulfonic acid and of at least one polymerization inhibitor and in the presence of at least one solvent selected from the group consisting of an aliphatic hydrocarbon, a cycloaliphatic hydrocarbon, and an aromatic hydrocarbon, which forms an azeotrope with water, the azeotrope is distilled off and condensed during the reacting, and the condensate splits into an aqueous phase and an organic phase to obtain a crude product,
wherein the reaction is performed in a reactor with a circulation evaporator,
wherein the organic phase is not returned to the reactor during the reacting, and
wherein the crude product is purified by distillation via at least one of a rectification column and a thin-film evaporator.

2. The process according to claim 1, wherein the isomer mixture of $C_{10}$-alcohols comprises from 60 to 98% by weight of 2-propylheptanol, from 1 to 15% by weight of 2-propyl-4-methylhexanol, from 0.01 to 20% by weight of 2-propyl-5-methylhexanol and from 0.01 to 24% by weight of 2-isopropylheptanol, where the sum of the proportions of the individual constituents does not exceed 100% by weight.

3. The process according to claim 1, wherein the isomer mixture of $C_{10}$-alcohols comprises from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol and from 0.1 to 2% by weight of 2 isopropyl-5-methylhexanol, where the sum of the proportions of the individual constituents does not exceed 100% by weight.

4. The process according to claim 1, wherein the purifying distillation is carried out at a bottom temperature of 100-140° C. and a top pressure of from 1 to 100 mbar.

5. The process according to claim 1, wherein the purifying distillation is carried out at a bottom temperature of 110-130° C. and a top pressure of from 1 to 50 mbar.

6. The process according to claim 1, wherein, in the purifying distillation, a portion of the condensate is fed back to the column as reflux.

7. The process according to claim 1, wherein the polymerization inhibitor is at least one compound selected from the group consisting of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2 methyl-4-tert-butylphenol, hypophosphorous acid, copper acetate, copper(II) chloride, copper salicylate and cerium(III) acetate.

8. The process according to claim 1, wherein the polymerization inhibitor is a copper salt.

9. The process according to claim 8, further comprising:
washing the crude product with an aqueous salt solution.

10. The process according to claim 9, wherein the washing is carried out concurrently with a neutralizing.

11. A batchwise process for preparing a mixture of $C_{10}$-alcohol (meth)acrylate esters, comprising:
reacting a (meth)acrylic acid with a $C_{10}$-alcohol mixture comprising 2-propylheptanol, and at least one selected from the group consisting of 2-propyl-4-methylhexanol, 2-propyl-5-methylhexanol, 2-isopropylheptanol, 2-isopropyl-4-methylhexanol, 2-isopropyl-5-methylhexanol and 2-propyl-4,4-dimethylpentanol,
wherein the reacting is carried out in a reactor having a circulation evaporator and in the presence of (i) at least one acidic catalyst selected from the group consisting of a mineral acid and a sulfonic acid, (ii) at least one polymerization inhibitor, and (iii) at least one solvent selected from the group consisting of an aliphatic hydrocarbon, a cycloaliphatic hydrocarbon, and an aromatic hydrocarbon, wherein the solvent forms a solvent:water azeotrope with water; and
wherein the reacting forms a reaction mixture comprising the $C_{10}$-alcohol (meth)acrylate esters, the solvent, the acidic catalyst, the polymerization inhibitor, the solvent:water azeotrope, and the water; then after the reacting,
distilling the solvent:water azeotrope from the reaction mixture and condensing a distillate to form a condensate which separates to form an aqueous phase and an organic phase, and wherein the distilling forms a crude product comprising the $C_{10}$-alcohol (meth)acrylate esters and wherein the organic phase is not returned to the reactor during the reacting;
distilling the crude product via at least one of a rectification column and a thin-film evaporator to obtain the mixture of $C_{10}$-alcohol (meth)acrylate esters in purified form.

12. The process according to claim 11, wherein the $C_{10}$-alcohol mixture comprises from 60 to 98% by weight of 2-propylheptanol, from 1 to 15% by weight of 2-propyl-4-methylhexanol, from 0.01 to 20% by weight of 2-propyl-5-methylhexanol and from 0.01 to 24% by weight of 2-isopropylheptanol, wherein the sum of the proportions of the 2-propylheptanol, the 2-propyl-4-methylhexanol, the 2-propyl-5-methylhexanol and the 2-isopropylheptanol does not exceed 100% by weight.

13. The process according to claim 11, wherein the $C_{10}$-alcohol mixture comprises from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol and from 0.1 to 2% by weight of 2 isopropyl-5-methylhexanol, wherein the sum of the proportions of the 2-propyl-4-methylhexanol, the 2-propyl-5-methylhexanol, the 2-isopropylheptanol, the 2-isopropyl-4-methylhexanol and the 2 isopropyl-5-methylhexanol does not exceed 100% by weight.

14. The process according to claim 11, wherein the solvent: water azeotrope is distilled at a bottom temperature of 100-140° C. and a top pressure of from 1 to 100 mbar.

15. The process according to claim 11, wherein the solvent: water azeotrope is distilled at a bottom temperature of 110-130° C. and a top pressure of from 1 to 50 mbar.

16. The process according to claim 11, wherein, during the distilling of the solvent:water azeotrope, a portion of the condensate is fed back to the column as reflux.

17. The process according to claim 11, wherein the polymerization inhibitor comprises at least one compound selected from the group consisting of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2 methyl-4-tert-butylphenol, hypophosphorous acid and cerium(III) acetate.

18. The process according to claim 11, wherein the polymerization inhibitor is a copper salt.

19. The process according to claim 11, further comprising: washing the crude product with an aqueous salt solution.

20. The process according to claim 19, wherein the washing is carried out concurrently with a neutralizing.

21. The process according to claim 1, wherein the organic phase is at least partly recycled as reflux to at least one of the rectification column and the thin-film evaporator during the reacting.

22. The process according to claim 11, wherein the organic phase is at least partly recycled as reflux to at least one of the rectification column and the thin-film evaporator during the reacting.

23. The process according to claim 1, wherein the solvent is not returned to the reactor during the reacting.

24. The process according to claim 11, wherein the solvent is not returned to the reactor during the reacting.

25. The process according to claim 1, wherein the reacting to form the crude product is carried out concurrently while the crude product is purified by distillation.

26. The process according to claim 1, wherein the crude product is purified by distillation via at least one of a rectification column and a thin-film evaporator subsequent to the reacting.

* * * * *